Figure 1:
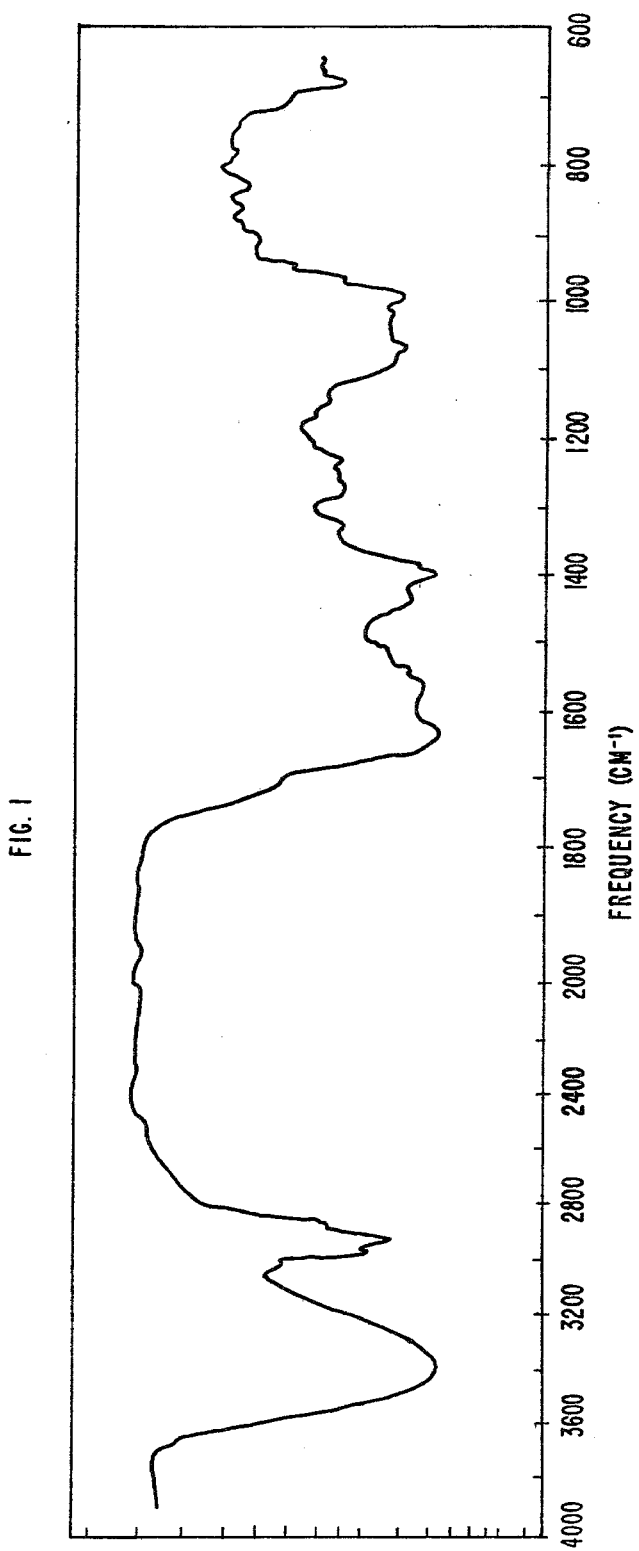

United States Patent [19]

Hernandez et al.

[11] 4,311,693

[45] Jan. 19, 1982

[54] DISCOVERY OF MSD A63A, A NEW EFROTOMYCIN-LINE ANTIBIOTIC FERMENTATION BROTH

[75] Inventors: Sebastian Hernandez, Madrid, Spain; Sheldon B. Zimmerman, Springfield, N.J.; Vincent P. Gullo, Edison, N.J.; Ray S. Dewey, Martinsville, N.J.

[73] Assignee: Merck & Co., Inc., Rahway, N.J.

[21] Appl. No.: 207,575

[22] Filed: Nov. 17, 1980

[51] Int. Cl.³ ............................................. A61K 35/00
[52] U.S. Cl. ................................... 424/122; 435/169; 435/170
[58] Field of Search ................. 435/169, 170; 424/122

Primary Examiner—Jerome D. Goldberg
Attorney, Agent, or Firm—Frank M. Mahon; Hesna J. Pfeiffer

[57] ABSTRACT

The antibiotic MSD A63A, having antibacterial and growth-permittant activity, is produced by fermentation of *Streptoverticillum hiroshimense* MA4845 (ATCC 31586), in a suitable nutrient media.

4 Claims, 2 Drawing Figures

DISCOVERY OF MSD A63A, A NEW EFROTOMYCIN-LINE ANTIBIOTIC FERMENTATION BROTH

This invention relates to a new anti-bacterial and growth-permittant antibiotic agent. More particularly, the instant invention relates to a new anti-bacterial and growth-permittant antibiotic agent, MSD A63A, hereinafter referred to as A63A. The invention encompasses the antibiotic in dilute forms; as crude concentrates; in pure forms; and in formulations suitable for antibiotic and growth-permittant applications.

It is an object of the instant invention to provide a new and useful antibiotic agent with anti-bacterial activity and growth-permittant activity. Another object is to provide a process for preparing the novel antibiotic substance by fermentation of a nutrient medium with a microorganism identified as *Streptoverticillium hiroshimense* MA4845 (ATCC 31586). Other objects will be apparent from the detailed description of the instant invention hereinafter provided.

In its composition of matter aspect, therefore, the instant invention may be described as residing in the concept of the novel antibiotic A63A having the physical and chemical characteristics hereinafter described. The instant invention is based upon applicants' discovery that A63A is an antibiotic which is effective against selected gram-positive and gram-negative bacteria and may be used to treat bacterial infections in animals. Furthermore, A63A may be used as a growth-permitting agent for animals such as chickens and pigs. It is contemplated that therapeutically effective amounts of antibiotic A63A will be employed in antibacterial and growth-permittant applications. The antibacterial and growth-permittant activity of antibiotic A63A have been confirmed by standard pharmacological techniques.

Antibiotic A63A is obtained by growing under controlled conditions the microorganism, *Streptoverticillium hiroshimense*, in a fermentation broth. The fermentation may be carried out in media containing suspended nutrient matter or in predominantly clear media wherein the medium is substantially free of suspended nutrient matter.

Based on extensive taxonomic studies, the A63A producing microorganism is identified as *Streptoverticillium hiroshimense* and is designated MA4845 in the culture collection of MERCK & CO., Inc., Rahway, N.J. A culture thereof has been placed on permanent deposit with the culture collection of the American Type Culture Collection, 12301 Parklawn Drive, Rockville, Maryland 20852 and has been assigned Accession No. ATCC 31586). Classification keys and culture descriptions of *Streptoverticillium hiroshimense* in standard taxonomic references show close morphological and culture characteristics with the A63A producing culture MA4845.

Morphological and cultural characteristics of *Streptoverticillum hiroshimense* MA4845 are set forth below.

MORPHOLOGICAL AND CULTURAL CHARACTERISTICS OF *STREPTOVERTICILLIUM HIROSHIMENSE* MA4845 (ATCC 31586)

Morphology:
Sporophores form short branches produced in a verticil or whorl at interverals along the aerial mycelium. These branches in turn produce several secondary branches that form straight chains of approximately 10–15 spores. Spores are cylindrical, $0.9\mu \times 1.2$–$7\mu$ (970X). Spore surface as seen by electron microscopy is smooth.

Cultural Characteristics:
(V=vegetative growth; A=aerial mycelium; SP=soluble pigment)

Oatmeal agar (ISP Medium 3)
V: Reverse—dark reddish brown
A: Velvety, rose beige (4ec); areas of white and rose-beige with a strong pink-tone.
SP: Dark reddish-brown Czapek Dox agar (sucrose nitrate agar)
V: Moderate, colorless
A: Sparse, pinkish
SP: None Egg albumin agar
V: colorless
A: Moderate, light rose-beige with strong pink tone
SP: None Glycerol asparagine agar (ISP Medium 5)
V: Reverse—reddish brown
A: Velvety, rose-beige (4ec); areas of a deeper rose-beige and areas with strong pink tone Inorganic salts-starch agar (ISP Medium 4)
V: Reverse—dark reddish brown with
A: Velvety, rose-beige (4ec) edged areas of rose-beige with strong pink tone.
SP: Light reddish brown Yeast extract-dextrose+salts agar
V: Dark reddish-brown
A: Sparse, pinkish white
SP: Reddish brown Yeast extract-malt extract agar (ISP Medium 2)
V: Reverse—dark reddish-brown
A: Velvety, rose-beige (4ec)
SP: Light reddish brown Peptone-iron-yeast extract agar
V: Tan
A: None
SP: Some browning of medium Nutrient tyrosine agar
V: Brown
A: None
SP: Brown
Decomposition of tyrosine: Positive Nutrient starch agar
V: Tan edged with red
A: None
SP: Light brown
Hydrolysis of starch—Moderate Nutrient gelatin agar
V: Tan edged with red
A: None
SP: Light brown
Liquefaction of gelatin—good Skim milk agar
V: Tan
A: None
SP: Very light tan
Hydrolysis if casein: Positive Litmus milk
V: Brown growth ring
A: None
Coagulation and/or peptonization:Peptonization becoming alkaline Carbon utilization Pridham-Gottlieb basal medium + 2% carbon source
+ = growth; ± = growth poor or questionable;
— = no growth as compared to negative control
(no carbon source)

| | |
|---|---|
| Glucose | + |
| Arabinose | — |
| Cellulose | — |
| Fructose | + |
| Inositol | + |
| Lactose | + |
| Maltose | + |
| Mannitol | — |
| Mannose | + |
| Raffinose | — |
| Rhamnose | — |
| Sucrose | ± |
| Xylose | — |

Temperature range: (Yeast extract-dextrose+salts agar)
28° C.—Good growth with sporulation
37° C.—Moderate vegetative growth
50° C.—No growth Oxygen requirement (Stab culture in yeast extract-dextrose+salts agar)
Aerobic All readings taken after three weeks at 28° C. unless noted otherwise. pH of all media approximately neutral (6.8–7.2)

Color number designations taken from Color Harmony Manual, 1958, 4th Edition, Container Corporation of America, Chicago, Ill.

ISP Media (International Streptomycete Project Media) are standard media described in the International Journal of Systematic Bacteriology, 16, 313 (1966)

Streptoverticillium hiroshimense MA4845 is simply illustrative of the type of strain of microorganism which can be used in the production of A63A and it should be understood that the present invention is not limited to organisms meeting these particular descriptions. This invention includes the use of the other microorganisms, including strains either isolated from nature or obtained by mutation as, for example, those obtained by natural selection or those produced by mutating agents, for example, X-ray irradiation, ultraviolet irradiation, nitrogen mustards and the like which, under suitable conditions will yield A63A.

PREPARATION OF ANTIBIOTIC A63A

A63A is produced during the aerobic fermentation of suitable aqueous nutrient media under controlled conditions via the inoculation with the organism Streptoverticillium hiroshimense MA4845. Aqueous media, such as those employed for the production of other antibiotics are suitable for producing the antibiotic A63A. Such media contain sources of carbon, nitrogen and inorganic salts assimilable by the microorganism. The choice of media is not critical and the fermentation may be carried out in media containing suspended nutrient matter or predominantly clear media wherein the media is substantially free of suspended nutrient matter.

In general, carbohydrates such as sugars, for example, dextrose, glucose, arabinose, maltose, raffinose, xylose, mannitol and the like and starches such as grains, for example, oats, rye, corn starch, corn meal, potato and the like can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 1% and 6% by weight of the medium. These carbon sources can be used individually, or several such carbon sources may be combined in the medium. In general, many proteinaceous materials may be used as nitrogen sources in the fermentation process. Suitable nitrogen sources include, for example, nutrient broth, yeast extract, yeast hydroylsates, primary yeast, soybean meal, cottonseed flour, hydrolysates of casein, corn steep liquor, distiller's solubles or tomatoe paste and the like. The sources of nitrogen, either alone or in combination, are used in amounts ranging from about 0.2% to 6% by weight of the aqueous medium.

The fermentation is carried out at temperatures ranging from about 20° C. to 37° C.; however, for optimum results it is preferable to conduct the fermentation at temperatures of from about 24° C. to 32° C. The pH of the nutrient media suitable for growing the Streptoverticillium hiroshimense MA4845 culture and producing the antibiotic A63A should be in the range of from about 6.0 to 8.0.

A small scale fermentation of the antibiotic is conveniently carried out by inoculating a suitable nutrient medium with the antibiotic-producing culture and, after transfer to a production medium, permitting the fermentation to proceed at a constant temperature of about 28° C. on a shaker for several days. At the end of the incubation period, the antibiotic activity is isolated from the fermentation broth by techniques hereinafter described.

The small scale fermentation may be conducted in a sterilized flask via a one-, two-, three- or four-stage seed development. The nutrient medium for the seed stage may be any suitable combination of carbon and nitrogen sources. The seed flask is shaken in a constant temperature chamber at about 28° C. until maximum growth is completed (usually 2–4 days) and some of the resulting growth is used to inoculate either a second stage seed or the production medium. Intermediate stage seed flasks, when used, are developed in essentially the same manner; that is, part of the contents of the flask are used to inoculate either the next stage seed medium or the production medium. The inoculated production flasks are shaken at a constant temperature for several days (usually 3 to 5 days) and at the end of the incubation period the antibiotic A63A is isolated.

For large scale work, it is preferable to conduct the fermentation in suitable tanks provided with an agitator and a means of aerating the fermentation medium. According to this method, the nutrient medium is made up in the tank and sterilized by heating at temperatures of up to about 120° C. Upon cooling, the sterilized medium is inoculated with a previously grown seed of the producing culture, and the fermentation is permitted to proceed for a period of several days as, for example, from 3 to 5 days while agitating and/or aerating the nutrient medium and maintaining the temperature at about 28° C.

A preferred process for preparing A63A is set forth below.

Seed Stage

To 50 ml of seed medium (described below) in a baffled sterilized 250 ml Erlenmeyer flask, add the contents of a lyophilized tube of sterilized tube of Streptoverticillium hiroshimense MA4845. Incubate at 28° C.

and 220 rpm until maximum growth is completed (usually 2-4 days).

Seed Medium

| | | |
|---|---|---|
| Dextrose | 1.0 | gm |
| Soluble Starch | 10.0 | gm |
| Beef Extract | 3.0 | gm |
| Yeast Autolysate (Ardamine pH) | 5.0 | gm |
| NZ Amine E | 5.0 | gm |
| MgSO$_4$ . H$_2$O | 0.05 | gm |
| KH$_2$PO$_4$ | 0.182 | gm |
| Na$_2$HPO$_4$ | 0.19 | gm |
| CaCO$_3$ | 0.50 | gm |
| Distilled Water | 1000 | ml |
| pH 7.0-7.2 with NaOH | | |

Production Stage

Inoculate into 250 ml sterilized unbaffled Erlenmeyer flasks containing 40 ml. of production media (described below) 2 ml of the seed culture obtained above. Incubate at 28° C. and 220 rpm for 4 days.

Production Media

| | | |
|---|---|---|
| Tomato Paste | 40.0 | gm |
| Oat Flour | 15.0 | gm |
| Distilled Water | 1000 | ml |
| pH 6.0 with NaOH | | |

Samples of production flasks at 3 days and 4 days were assayed for antibacterial activity versus *Escherichia coli* by standard disk assay techniques with the following results.

| Zone of Inhibition (mm - ¼" disc) vs *Escherichia coli* | |
|---|---|
| 3 -Days | 4-Days |
| 13 | 15 |

Although the production media described above is a preferred media for the production of antibiotic A63A it is illustrative of how a wide variety of media may be employed. Typical of other useful media, for example, are the following:

Production Media

| | | |
|---|---|---|
| 1. Corn Steep Liquor | 15.0 | gm |
| (NH$_4$)$_2$SO$_4$ | 4.0 | gm |
| CaCO$_3$ | 6.0 | gm |
| CPC Industrial Starch Mod. (Corn Products Int.) (Englewood Cliffs, N.J.) | 20.0 | gm |
| Corn Meal | 1.0 | gm |
| Soybean Meal | 4.0 | gm |
| Dextrose | 5.0 | gm |
| KH$_2$PO$_4$ | 0.3 | gm |
| Soybean Oil | 2.5 | ml |
| Distilled Water | 1000 | ml |
| pH 6.7 | | |
| 2. Corn Meal | 20.0 | gm |
| Distillers Solubles | 10.0 | gm |
| Soybean Meal | 15.0 | gm |
| Sodium Citrate | 4.0 | gm |
| CaCl$_2$ . 2H$_2$O | 0.5 | gm |
| MgSO$_4$ . 7H$_2$O | 0.1 | gm |
| CoCl$_2$16H$_2$O | 0.01 | gm |
| FeSO$_4$ . 7H$_2$O | 0.01 | gm |
| Polyglycol P2000 (Dow Chemical Co.) | 2.5 | ml |

Production Media -continued

| | |
|---|---|
| (Midland, Michigan) Distilled Water | 1000 ml |
| pH 6.5 | |

ISOLATION OF ANTIBIOTIC A63A

Adjust 830 ml of whole broth, prepared as described above, from pH 6.2 to pH 9.0 with dilute aqueous sodium hydroxide. Filter through a Buchner funnel containing a Super-Cel (Johns-Manville, New York, N.Y.) pre-coat. Adsorb filtered broth onto an 85 ml bed (2.5 cm dia. ×20 cm. hgt.) of Amberlite XAD-2 resin (Rohm & Haas Co., Philadelphia, Pa.) during a 10 minute contact time. Elute with 170 ml of 60% aqueous acetone and concentrate the eluate to 100 ml in vacuo at 30° C. to remove acetone. Adjust the concentrate to pH 3.5 with dilute aqueous hydrochloric acid and extract twice with 100 ml portions of ethyl acetate. Combine the ethyl acetate extracts, dry over sodium sulfate, filter, and evaporate to dryness at 30° C. (yield: 80 mg partially thin-layer chromatography on pre-washed silica-gel plates developed in the solvent system, chloroform-methanol-conc. ammonium hydroxide (80:20:1) (yield: 2.7 mg).

PHYSICAL CHARACTERISTICS OF ANTIBIOTIC A63A

For characterization of the physical properties the above product was further fractionated by thin layer chromatography on silica gel with methylene chloride, methanol and concentrated aqueous ammonia (80:20:1). The material was eluted from the silica gel with methylene chloride, methanol and water (60:30:3). This solution was concentrated. The concentrate was taken up in benzene, 10% to 20% methanol, filtered and lyophilized. Antibiotic A63A is a slightly deliquescent amorphous yellow powder and is thought to be related to a previously described product, Antibiotic A40A, U.S. Ser. No. 74,202, filed Sept. 13, 1979. The mass spectra of the trimethylsilyl derivative showed well-defined peaks up to m/e 1122 and weak peaks up to about 1212. The estimated empirical formula is C$_{44}$H$_{64}$N$_2$O$_{10}$; calc. for C$_{44}$H$_{64}$N$_2$O$_{10}$−2H$_2$O+4C$_3$H$_8$Si, 1032.5906; found; 1032.5840. In addition, characteristic peaks are found at m/e 960, 706, 677, 604, 544, 517, 444 and 221. Weaker peaks seen at m/e 1120 and 1030 are attributed to minor impurities. The level of silylation is confirmed from spectra of the deutero analogs.

Antibiotic A63A showed an ultraviolet spectrum in methanol with maxima at 328 nm (E% 332), 286 (E% 289) and 224 (E% 757) with shoulders at 366 (E% 256) and 315 (E% 313). After 30 minutes in 0.01 N HCl in methanol, a characteristic spectrum developed which showed intense maxima at 324 nm (E% 440), 309 (E% 502 295 (E% 420) and 223 (E% 838) with shoulders at 365 (E% 121) and 284 (E% 339). The antibiotic shows a rotation of $a_D{}^{26°} = -43°$ for a 1% solution in methanol.

Figure 2:
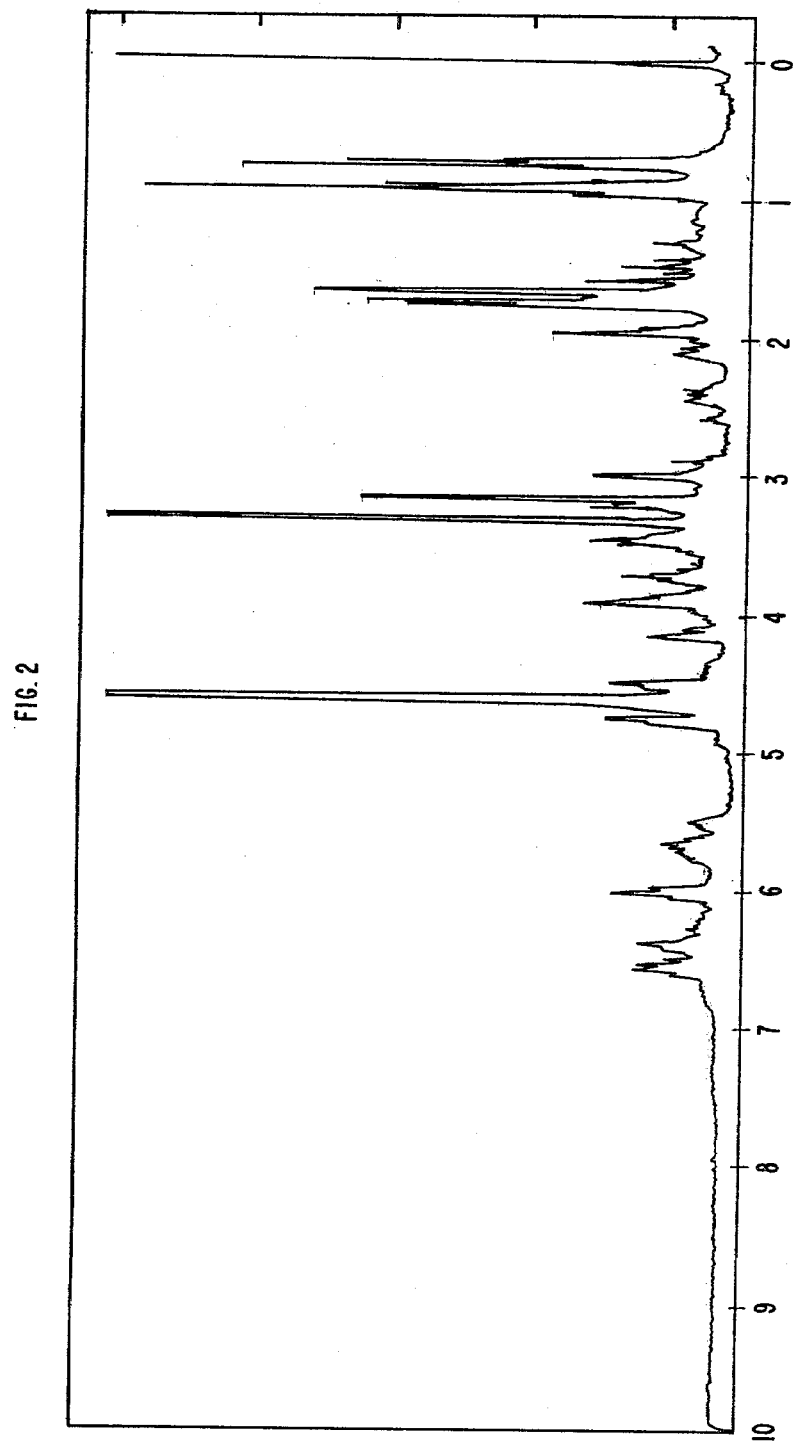

The infrared spectrum of a KBr mull was recorded on a Perkin Elmer Model 421 infrared spectrometer and is shown in FIG. 1. The $^1$H NMR spectrum in CD$_3$OD solution in the presence of saturated bicarbonate, with tetramethylsilane as internal standard, was recorded on a Varian SC 300 NMR spectrometer and is shown in FIG. 2; the peaks at 3.32 and 4.60 and their sidebands are attributed to solvent impurities.

BIOLOGICAL CHARACTERISTICS OF ANTIBIOTIC A63A

A. Antibacterial Activity

Antibiotic A63A shows activity against selected gram-positive and gram-negative bacteria. In vitro, when assayed by standard disc-plate techniques (¼ inch antibiotic saturated discs assayed against nutrient agars seeded with test organisms). A63A is effective at 300 μ/ml against *Sarcina lutea* ATCC 9341, *Brucella bronchiseptica* ATCC 4617, *Vibrio percolans* ATCC 8461, *Corynebacterium pseudoiphtheriticium* ATCC 9742, *Streptococcus faecium* MB 2820, *Streptococcus agalactiae* MB 2875, *Micrococcus luteus* MB 369. At 1000 μg/ml antibiotic A63A is also effective against *Bacillus* sp MB 633, *Salmonella gallinarum* MB 1287, *Xanthomonas vesicatoria* MB 815, *Proteus vulgaris* ATCC 21100, *Pseudomonas stutzeri* ATCC 11607, *Klebsiella pneumoniae* MB 1264, *Aerobacter aerogenes* MB 835, *Erwinia atroseptica* ATCC 4446, *Proteus vulgaris* ATCC 21100 (with episome) and *Proteus mirabilis* MB 3126.

When used as an antibiotic, A63A may be employed in the form of pharmaceutical preparations which contain it in admixture or conjunction with an organic or inorganic, solid or liquid pharmaceutical excipient suitable for enteral, parenteral or local administration. Suitable excipients are substances that do not react with the antibiotic, for example, water, gelatin lactose, starches, stearyl alcohol, magnesium stearate, talcum, vegetable oils, benzyl alcohols, gums, propyleneglycols, polyalkyleneglycols, white petroleum jelly, cholesterol or other known medicinal excipients. The pharmaceutical preparations may be, for example, tablets, dragees, ointments, creams or capsules, or in liquid form solutions, suspensions or emulsions. They may be sterilized and/or contain assistants, such as preserving, stabilizing, wetting or emulsifying agents; solution promoters, salts for regulating the osmotic pressure or buffers.

Where it is desired to administer the antibiotic in dry, solid unit dosage form, capsules, boluses or tablets containing the desired amount of antibiotic are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of A63A depending upon factors such as the type of host animal to be treated, the severity and type of infection and the weight of the host. The antibiotic may be administered on a daily basis at from about 5 to 100 mg per kilograms of body weight.

B. Growth Permittant Activity

In order to evaluate the growth-permittant activity of antibiotic A63A, the antibiotic was tested in chicks by the technique described below.

Procedure

Day-old Hubbard-Hubbard male chickens were received from a commercial hatchery and housed in an electrically-heated battery in a temperature-controlled room. Immediately on arrival the birds were fed a commercial corn-soybean chick starter diet containing no medication. At 4 days of age, the birds were individually weighed and those in the middle of the weight distribution were randomly assigned to the experimental pens on an equal weight basis. The experimental birds were then fed a semipurified soybean protein-sucrose based diet containing either no medication or 5 ppm, 10 ppm or 20 ppm of one of the test ingredients. Each treatment was fed to replicate pens of 8 chickens per pen for the 10-day experimental period. Six replicate pens served as the nonmedicated controls. Weights of the individual birds were recorded at the beginning, at 5 days on test and at the conclusion of the experiment. The feed consumption per pen was recorded during the experimental period.

Results

The average relative percent weight gain and feed efficiency of each treatment group is presented in Table 1. Feeding graded levels of A63A resulted in dose-related responses.

The chicks used in this experiment were from a breeder flock just coming into production. Therefore, their average size at the start of the experiment was small, which has a tendency to result in slightly larger growth responses than normally expected. Also, the stress of placing these small birds on the semipurified diet is reflected by the mortality rates.

TABLE 1

Effect of feed A63A on weight gain and feed efficiency of broiler male chickens fed a semi-purified diet

| Dietary Treatment | | Results of a 10-day Test | | |
|---|---|---|---|---|
| | | No. Chicks Dead/Total | Weight Gain | Feed /Gain |
| ppm | | | (Rel. %) | (Rel. %) |
| | None | 1/48 | 88.2 g | 1.894 g/g |
| 5 | A63A | 3/16 | +4.2 | −4.4 |
| 10 | " | 2/16 | +11.3 | −10.2 |
| 20 | " | 1/16 | +13.4 | −9.9 |

Thus it is clear that antibiotic A63A displays significant growth-permittant activity; i.e. effective in permitting an animal to growth toward its full genetic potential. A63A, therefore may be used as a feed additive to permit the growth of monogastric animals such as chickens and swine. When so used, A63A shortens the time required for bringing animals up to marketable weight.

When A63A is used as a growth-permittant in animals, it can be administered as a component of the feed of the animals or may be suspended in the drinking water.

When A63A is used as a component of animal feed, it is first formulated as a feed supplement. In such feed supplements, A63A is present in relatively concentrated amounts intimately dispersed in an inert carrier or diluent. The feed supplement can be added to the feed or made into a premix by an intermediate dilution or blending step. By inert carrier is meant one that will not react with the antibiotic and one that may be administered safely to animals. Preferably, the carrier is one that is, or may be, an ingredient of the animal ration. Typical carriers or diluents suitable for such compositions include, for example, distillers' dried grains, corn meal, citrus meal, fermentation residues, ground oyster shells, wheat shorts, molasses solubles corn cob meal, edible bean mill feed, soya grits, crushed limestone and the like.

The antibiotic is intimately dispersed throughout the carrier by methods such as grinding, sitrring, milling or tumbling. Compositions containing from about 50,000 to 500,000 ppm of the antibiotic are particularly suitable as feed supplements.

Examples of typical feed suppliments containing A63A dispersed in a solid carrier are:

| (A) A63A | 5 |
|---|---|
| Wheat Standard Middling | 95 |
| (B) A63A | 50 |
| Corn distillers' grains | 50 |

These and similar feed supplements are prepared by uniformly mixing the antibiotic with the carrier.

The feed supplement can be added directly to the feed or made into a premix by an intermediate dilution or blending step with an orally ingestable carrier. Compositions containing 300 to 5000 ppm of the antibiotic are particularly suitable as premixes. These premixes are prepared by uniformly mixing the antibiotic with an orally ingestable carrier.

Such supplements or premixes are added to the animal feed in an amount to give the finished feed the concentration of A63A desired for growth permittant activity. In chickens, A63A is fed at a final concentration of between 10–100 ppm of feed in order to achieve the desired growth permitting result. In the case of swine, including swine infected with Mycoplasma, (PPLO), for example, *Mycoplasma hyorhinis,* A63A may be administered in the feed at similar levels.

In the above discussion of this invention, emphasis has been placed on solid compositions wherein the A63A is mixed with an edible carrier in a feed supplement, in a so-called premix or in the final feedstuff. This is the preferred method of administering the A63A. An alternate method is to suspend the A63A in the drinking water of the animals. The quantity that may be suspended in the water without undue settling is limited. Emulsifiers or surface-active agents may be employed for this latter purpose.

It will likewise be understood by those skilled in this art that special feed supplement formulations and finished animal feeds containing A63A may also include vitamins, other antibiotics and growth-permitting agents and other nutritional substances.

A63A is useful against poultry mycoplasmal infections in a range of 5 to 100 mg/kg. A preferred range for a single dose is from 35 to 50 mg./kg. For reasons of convenience a preferred method of administering the antibiotic in the treatment of mycoplasmal infections is to admix the A63A with the animal feed. A preferred range for PPLO is from 50 to 200 ppm of feed.

In the treatment of air sacculitis in broilers, the $ED_{50}$ is 40 to 100 mg./kg. Accordingly, a useful dosage of A63A may vary from 10 to 150 mg./kg.

A solution or suspension for subcutaneous injection for treatment of air sacculitis in broilers may be prepared as follows:

| Subcutaneous Suspension Containing 20 mg. of A63A Ampoule: | |
|---|---|
| A63A | 20 mg. |
| Diluent: Sterile water for injection | 2 cc. |

Included in this invention are the non-toxic, pharmaceutically acceptable salts of A63A, for example the alkali and alkaline earth metal salts such as those derived from sodium, potassium, ammonium and calcium or salts with organic bases, for example, triethylamine, N-ethylpiperidine, dibenzylethylendiamine.

The subject matter which applicants regard as their invention is particularly pointed out and distinctly claimed as follows:

1. The antibiotic MSD A63A which is a slightly deliquescent amorphous yellow powder having an estimated empirical formula of $C_{44}H_{64}N_2O_{10}$ whose trimethylsilyl derivative shows characteristic peaks in its mass spectrum at m/e 1122, 1032, 960, 706, 677, 604, 544, 517, 444 and 221; which shows an ultraviolet spectrum in methanol with maxima at 328 nm (E% 332), 286 (E% 289) and 224 (E% 757) with shoulders at 366 (E% 256) and 315 (E% 313) and which develops a characteristic spectrum after 30 minutes in 0.01 N hydrochloric acid in methanol which shows maxima at 324 nm (E% 440), 309 (E% 502), 295 (E% 420) and 223 (E% 838) with shoulders at 365 (E% 121) and 284 (E% 339); which shows a rotation of $\alpha_D{}^{26°} = -43°$ for a 1% solution in methanol; which has an infrared spectrum as shown in FIG. 1; and an $^1H$ NMR spectrum as shown in FIG. 2.

2. A method of producing antibiotic MSD A63A as defined in claim 1 which comprises cultivating an MSD A63A producing strain of *Streptoverticillium hiroshimense* ATCC 31586 in a fermentation broth containing assimilable sources of carbohydrates, nitrogen and inorganic salts under aerobic conditions until a substantial amount of MSD A63A is produced in the fermentation broth and recovering said antibiotic.

3. An antibacterial composition comprising an antibacterially effective amount of MSD A63A as defined in claim 1 or a pharmaceutically acceptable salt thereof and a pharmaceutically acceptable carrier.

4. A growth-permittant composition comprising a growth-permitting amount of MSD A63A as defined in claim 1 or a pharmaceutically acceptable salt thereof and a pharmaceutically acceptable carrier.

* * * * *